(12) United States Patent
Toyoda et al.

(10) Patent No.: US 11,090,405 B2
(45) Date of Patent: Aug. 17, 2021

(54) LAMINATE PATCHABLE TO LIVING BODY

(71) Applicant: NITTO DENKO CORPORATION, Osaka (JP)

(72) Inventors: Eiji Toyoda, Osaka (JP); Ryoma Yoshioka, Osaka (JP); Naoya Sugimoto, Osaka (JP); Yu Tachikawa, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 16/333,432

(22) PCT Filed: Aug. 10, 2017

(86) PCT No.: PCT/JP2017/029069
§ 371 (c)(1),
(2) Date: Mar. 14, 2019

(87) PCT Pub. No.: WO2018/051694
PCT Pub. Date: Mar. 22, 2018

(65) Prior Publication Data
US 2019/0247534 A1    Aug. 15, 2019

(30) Foreign Application Priority Data
Sep. 15, 2016    (JP) .............................. JP2016-180411

(51) Int. Cl.
| | | |
|---|---|---|
| A61L 15/20 | (2006.01) | |
| A61K 47/14 | (2017.01) | |
| A61K 47/32 | (2006.01) | |
| A61K 9/70 | (2006.01) | |
| A61L 15/24 | (2006.01) | |
| A61L 15/26 | (2006.01) | |
| C09J 11/06 | (2006.01) | |
| C09J 201/00 | (2006.01) | |
| C09J 7/20 | (2018.01) | |

(52) U.S. Cl.
CPC ................ *A61L 15/20* (2013.01); *A61K 9/70* (2013.01); *A61K 47/14* (2013.01); *A61K 47/32* (2013.01); *A61L 15/24* (2013.01); *A61L 15/26* (2013.01); *C09J 7/20* (2018.01); *C09J 11/06* (2013.01); *C09J 201/00* (2013.01)

(58) Field of Classification Search
CPC .......... A61L 15/20; A61L 15/26; A61L 15/24; A61L 15/34; A61L 15/42; A61L 15/585; C09J 7/20; C09J 201/00; C09J 11/06; C09J 2205/106; C09J 2205/102; C09J 7/38; C09J 2301/41; C09J 2301/408; A61K 9/70; A61K 47/32; A61K 47/14; C08K 5/10
See application file for complete search history.

(56) References Cited

U.S. PATENT DOCUMENTS

| | | | |
|---|---|---|---|
| 8,597,774 B2 | 12/2013 | Fukue et al. | |
| 2003/0124343 A1* | 7/2003 | Murakami | ............... A61L 15/24 428/343 |
| 2003/0224160 A1* | 12/2003 | Murakami | ............... A61L 15/58 428/343 |

FOREIGN PATENT DOCUMENTS

| | | |
|---|---|---|
| JP | 2003-190205 A | 7/2003 |
| JP | 2003-342541 A | 12/2003 |
| JP | 2009-083185 A | 4/2009 |
| JP | 4905612 B2 | 3/2012 |
| JP | 2012-508984 A | 4/2012 |
| WO | 2010/056857 A2 | 5/2010 |
| WO | 2012/008278 A1 | 1/2012 |

OTHER PUBLICATIONS

International Preliminary Report on Patentability issued by WIPO dated Mar. 19, 2019, in connection with International Patent Application No. PCT/JP2017/029069.
International Search Report Issued in PCT/JP2017/029069 dated Sep. 26, 2017.
Written Opinion Issued in PCT/JP2017/029069 dated Sep. 26, 2017.
Office Action, issued by the Japanese Patent Office dated Aug. 12, 2020, in connection with Japanese Patent Application No. 2016-180411.
Office Action, issued by the Japanese Patent Office dated Mar. 4, 2021, in connection with Japanese Patent Application No. 2016-180411.

* cited by examiner

*Primary Examiner* — Snigdha Maewall
(74) *Attorney, Agent, or Firm* — Edwards Neils LLC; Jean C. Edwards, Esq.

(57) ABSTRACT

A laminate patchable to a living body and that includes a pressure-sensitive adhesive layer for patching to the living body and a substrate layer disposed on a one-side surface in a thickness direction of the pressure-sensitive adhesive layer and supporting the pressure-sensitive adhesive layer. The pressure-sensitive adhesive layer contains a first carboxylic acid ester and the substrate layer contains a second carboxylic acid ester.

4 Claims, 2 Drawing Sheets

FIG. 3
Example 1

FIG. 4
Comparative Example 1

LAMINATE PATCHABLE TO LIVING BODY

CROSS-REFERENCE TO RELATED APPLICATIONS

The present application is a 35 U.S.C. 371 National Stage Entry of PCT/JP2017/029069, filed on Aug. 10, 2017, which claims priority from Japanese Patent Application No. 2016-180411, filed on Sep. 15, 2016, the contents of all of which are herein incorporated by reference in their entirety.

TECHNICAL FIELD

The present invention relates to a laminate patchable to a living body, to be specific, to a laminate patchable to a living body used for various uses such as medical use and sanitary material use.

BACKGROUND ART

Conventionally, it has been known that various pressure-sensitive adhesion tapes are used for medical use and sanitary material use. Those pressure-sensitive adhesion tapes are directly patched to the skin, so that they suppress physical stimuli given to the skin at the time of peeling, while having elasticity capable of conforming to a curved surface and movement of the skin.

For example, a pressure-sensitive adhesion sheet having a pressure-sensitive adhesion layer that is formed from a resin composition containing an acrylic ester polymer as a main component and a carboxylic acid ester added so as to be easily peeled from the skin on a film has been proposed (ref: for example, Patent Document 1).

CITATION LIST

Patent Document

Patent Document 1: Japanese Unexamined Patent Publication No. 2003-342541

SUMMARY OF THE INVENTION

Problem to be Solved by the Invention

However, in the pressure-sensitive adhesion sheet including Patent Document 1, there is a disadvantage that the film is deformed by heating in accordance with its use.

The present inventors considered the disadvantage and found new knowledge that a carboxylic acid ester is transferred into the film to deform the film, so that research has been further conducted to reach the completion of the present invention.

Means for Solving the Problem

The present invention (1) includes a laminate patchable to a living body including a pressure-sensitive adhesive layer for patching to the living body and a substrate layer disposed on a one-side surface in a thickness direction of the pressure-sensitive adhesive layer and supporting the pressure-sensitive adhesive layer, wherein the pressure-sensitive adhesive layer contains a first carboxylic acid ester and the substrate layer contains a second carboxylic acid ester.

In the laminate patchable to a living body, the substrate layer contains the second carboxylic acid ester, so that when the laminate patchable to a living body is heated, a transfer of the first carboxylic acid ester from the pressure-sensitive adhesive layer to the substrate layer can be suppressed. Thus, deformation of the substrate layer caused by the transfer of the first carboxylic acid ester to the substrate layer can be suppressed. As a result, the laminate patchable to a living body has excellent heat resistance.

The present invention (2) includes the laminate patchable to a living body described in (1), wherein the ratio (A/B) of a content ratio A of the second carboxylic acid ester with respect to the substrate layer to a content ratio B of the first carboxylic acid ester with respect to the pressure-sensitive adhesive layer is 0.1 or more and 0.5 or less.

In the laminate patchable to a living body, the ratio (A/B) of the content ratio A of the second carboxylic acid ester with respect to the substrate layer to the content ratio B of the first carboxylic acid ester with respect to the pressure-sensitive adhesive layer is 0.1 or more, so that when the laminate patchable to a living body is heated, the transfer of the first carboxylic acid ester from the pressure-sensitive adhesive layer to the substrate layer can be furthermore suppressed. Thus, the laminate patchable to a living body has further more excellent heat resistance.

Also, the ratio (A/B) is 0.5 or less, so that occurrence of bleeding (precipitation) of the second carboxylic acid ester on a surface of the substrate layer is suppressed, and contamination toward the periphery caused by the bleeding (precipitation) and sticking of the substrate layer to the periphery can be suppressed.

The present invention (3) includes the laminate patchable to a living body described in (1) or (2), wherein the content ratio A of the second carboxylic acid ester with respect to the substrate layer is 5 mass % or more.

In the laminate patchable to a living body, the content ratio A of the second carboxylic acid ester with respect to the substrate layer is 5 mass % or more, so that when the laminate patchable to a living body is heated, the transfer of the first carboxylic acid ester from the pressure-sensitive adhesive layer to the substrate layer can be furthermore suppressed. Thus, the laminate patchable to a living body has further more excellent heat resistance.

The present invention (4) includes the laminate patchable to a living body described in any one of (1) to (3), wherein the first carboxylic acid ester and the second carboxylic acid ester are a glyceryl trifatty acid ester.

In the laminate patchable to a living body, the first carboxylic acid ester and the second carboxylic acid ester are the glyceryl trifatty acid ester, so that stimuli to the skin at the time of the peeling can be furthermore suppressed, and the heat resistance can be further improved.

The present invention (5) includes the laminate patchable to a living body described in any one of (1) to (4), wherein the thickness of the substrate layer is 1 µm or more and 3 mm or less.

In the laminate patchable to a living body, the thickness of the substrate layer is 1 µm or more, so that the shape of the substrate layer can be surely retained. Thus, the laminate patchable to a living body has excellent handleability. Also, the thickness of the substrate layer is 3 mm or less, so that the conformability of the substrate layer can be ensured, and the substrate layer can be surely patched to the living body. Also, inconvenience is hardly felt in a state of patching the laminate patchable to a living body to the skin.

The present invention (6) includes the laminate patchable to a living body described in any one of (1) to (5), wherein the ratio (X/Y) of a saponification value X of the second carboxylic acid ester to a saponification value Y of the first carboxylic acid ester is 0.5 or more and 2 or less.

In the laminate patchable to a living body, the ratio (X/Y) of the saponification value X of the second carboxylic acid ester to the saponification value Y of the first carboxylic acid ester is 0.5 or more and 2 or less, so that the properties of the second carboxylic acid ester are similar to or the same as those of the first carboxylic acid ester, and when the laminate patchable to a living body is heated, the transfer of the first carboxylic acid ester from the pressure-sensitive adhesive layer to the substrate layer can be furthermore suppressed. Thus, the laminate patchable to a living body has further more excellent heat resistance.

Effect of the Invention

The laminate patchable to a living body of the present invention has excellent heat resistance.

DESCRIPTION OF EMBODIMENTS

1. Layer Structure of Laminate Patchable to Living Body

Figure 1:
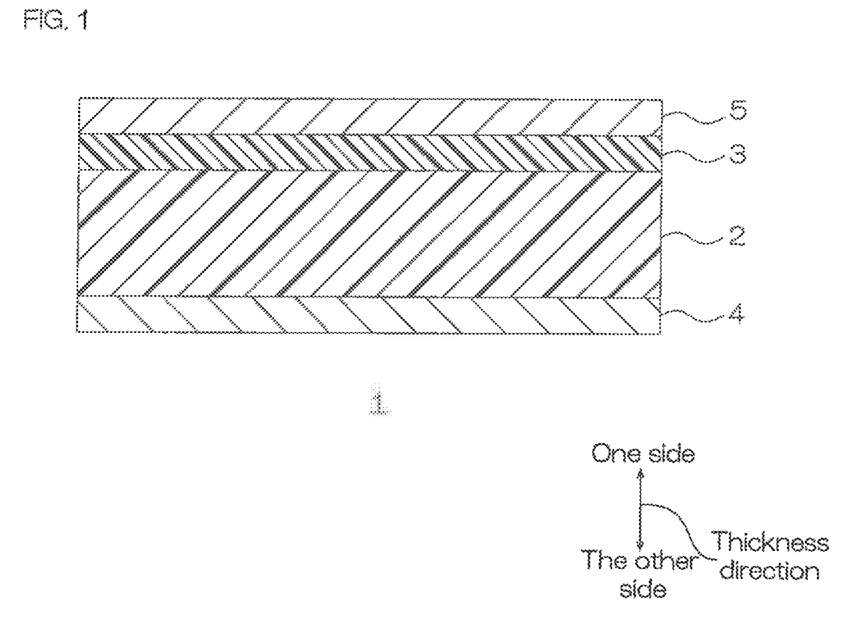
FIG. 1 shows a cross-sectional view of one embodiment (embodiment including a peeling layer and a backing film) of a laminate patchable to a living body of the present invention.

As shown in FIG. 1, a laminate patchable to a living body 1 that is one embodiment of the present invention includes, for example, a pressure-sensitive adhesive layer 2 and a substrate layer 3. The laminate patchable to a living body 1 also includes a peeling layer 4 and a backing film 5. To be specific, the laminate patchable to a living body 1 sequentially includes the peeling layer 4, the pressure-sensitive adhesive layer 2, the substrate layer 3, and the backing film 5 toward one side in a thickness direction. In the following, each layer is sequentially described.

2. Peeling Layer

The peeling layer 4 is the other-side layer in the thickness direction that forms the other-side surface in the thickness direction of the laminate patchable to a living body 1. The peeling layer 4 is a film that is used for fabricating the pressure-sensitive adhesive layer 2, and a peeling layer (protecting layer) that protects the pressure-sensitive adhesive layer 2 before the use of the laminate patchable to a living body 1 and is peeled from the pressure-sensitive adhesive layer 2 at the time of the use of the laminate patchable to a living body 1. The peeling layer 4 has a generally flat plate (sheet) shape extending in a plane direction (direction perpendicular to the thickness direction). Examples of the peeling layer 4 include resin films including polyester films such as polyethylene terephthalate (PET) film, polyethylene naphthalate film, and polybutylene terephthalate film and polyolefin films such as polyethylene, polypropylene, and polycylopentene. A surface of the peeling layer 4 may be subjected to peeling treatment. The thickness of the peeling layer 4 is, for example, 1 μm or more, preferably 10 μm or more, and for example, 100 μm or less, preferably 1000 μm or less.

3. Pressure-Sensitive Adhesive Layer

The pressure-sensitive adhesive layer 2 is a patch layer for patching the substrate layer 3 to be described later to a living body. The pressure-sensitive adhesive layer 2 is in contact with the entire one-side surface in the thickness direction of the peeling layer 4. The pressure-sensitive adhesive layer 2 has a generally flat plate (sheet) shape extending in the plane direction. The pressure-sensitive adhesive layer 2 is prepared from a pressure-sensitive adhesive composition.

The pressure-sensitive adhesive composition contains, for example, an acrylic polymer and a first carboxylic acid ester.

The acrylic polymer is a main component in the pressure-sensitive adhesive composition, and is, for example, a pressure-sensitive adhesive component. The acrylic polymer is a polymer obtained by polymerizing a monomer component containing a (meth)acrylate ester (to be specific, isononyl acrylate, methoxyethyl acrylate, or the like) as a main component (the content ratio thereof in the monomer component is 70 mass % or more and 99 mass % or less) and a monomer copolymerizable with the (meth)acrylate ester (to be specific, acrylic acid or the like) as an optional component (the content ratio thereof in the monomer component is 30 mass % or less and 1 mass % or more). An example of the acrylic polymer includes the acrylic polymer described in Japanese Unexamined Patent Publication No. 2003-342541.

The first carboxylic acid ester is a pressure-sensitive adhesive force adjusting agent that reduces the pressure-sensitive adhesive force of the acrylic polymer and adjusts the pressure-sensitive adhesive force of the pressure-sensitive adhesive layer 2 in the pressure-sensitive adhesive composition. The first carboxylic acid ester is a carboxylic acid ester that is compatible with the acrylic polymer.

The first carboxylic acid ester is, for example, an ester of a carboxylic acid and an alcohol.

An example of the carboxylic acid includes a fatty acid containing one carboxyl group in a molecule. Examples of the fatty acid include monocarboxylic acids including straight-chain saturated fatty acids having a carbon number of 5 or more and 22 or less such as valeric acid (pentanoic acid, carbon number of 5), caproic acid (hexanoic acid, carbon number of 6), enanthic acid (heptanoic acid, carbon number of 7), caprylic acid (octanoic acid, carbon number of 8), pelargonic acid (nonanoic acid, carbon number of 9), capric acid (decanoic acid, carbon number of 10), undecanoic acid (carbon number of 11), lauric acid (dodecanoic acid, carbon number of 12), myristic acid (tetradecanoic acid, carbon number of 14), palmitic acid (hexadecanoic acid, carbon number of 16), stearic acid (octadecanoic acid, carbon number of 18), and behenic acid (docosanoic acid, carbon number of 22); branched saturated fatty acids having a carbon number of 8 or more and 18 or less such as 2-ethyl hexanoic acid, dimethyloctanoic acid, and isostearic acid (2-heptyl undecanoic acid); and unsaturated fatty acids having a carbon number of 5 or more and 22 or less such as oleic acid, linolic acid, and linolenic acid.

Examples of the carboxylic acid also include polycarboxylic acids having two or more carboxyl groups in a molecule including dicarboxylic acids such as fumaric acid and phthalic acid. Furthermore, examples of the carboxylic acid include hydroxycarboxylic acids such as lactic acid.

As the carboxylic acid, preferably, a fatty acid having one carboxyl group in a molecule is used, more preferably, a straight-chain saturated fatty acid is used, further more preferably, a straight-chain saturated fatty acid having a carbon number of 6 or more and 18 or less is used, particularly preferably, a straight-chain saturated fatty acid having a carbon number of 8 or more and 16 or less is used, most preferably, a caprylic acid (carbon number of 8) and a myristic acid (carbon number of 14) are used.

Examples of the alcohol include monohydric alcohols and polyhydric alcohols.

Examples of the monohydric alcohol include methanol, ethanol, propanol, isopropanol, butanol, hexanol, octanol, decanol, cetyl alcohol (1-hexadecanol), isocetyl alcohol, myristyl alcohol (1-tetradecanol), and stearyl alcohol (1-octadecanol).

Examples of the polyhydric alcohol include dihydric alcohols such as ethylene glycol and propylene glycol, trihydric alcohols such as glycerin and trimethylolpropane, and tetrahydric alcohols such as pentaerythritol and diglycerine.

As the alcohol, preferably, a polyhydric alcohol is used, more preferably, a trihydric alcohol is used, further more preferably, a glycerin is used.

In the first carboxylic acid ester, when the alcohol is the polyhydric alcohol, a portion of the hydroxyl group in the polyhydric alcohol forms an ester bond, and the remaining portion can also remain as the hydroxyl group.

To be specific, an example of the first carboxylic acid ester includes an ester of a carboxylic acid (fatty acid) and a trihydric alcohol such as glyceryl tricaprylate, glyceryl monocaprylate, glyceryl tri-2-ethyl hexanoate, glyceryl tricaprate, glyceryl trilaurate, glyceryl triisostearate, glyceryl trioleate, and tri-2-ethylhexanoate trimethylolpropane. An example of the first carboxylic acid ester also includes an ester of a carboxylic acid and a dihydric alcohol such as propylene glycol dicaprylate, propylene glycol dicaprate, and propylene glycol diisostearate. An example of the first carboxylic acid ester also includes an ester of a carboxylic acid and a monohydric alcohol such as ethyl myristate, isopropyl myristate, isopropyl palmitate, butyl stearate, isopropyl isostearate, hexyl laurate, diethyl phthalate, dioctyl phthalate, stearyl myristate, stearyl oleate, cetyl dimethyloctanoate, cetyl 2-ethylhexanoate, isocetyl 2-ethylhexanoate, stearyl 2-ethylhexanoate, and dioctyl succinate. Furthermore, examples of the first carboxylic acid ester include cetyl lactate and myristyl lactate.

As the first carboxylic acid ester, preferably, an ester of a fatty acid and a trihydric alcohol is used, more preferably, in view of low irritating properties to the skin, compatibility with the acrylic polymer, or the like, an ester of a fatty acid and a glycerin (glyceryl trifatty acid ester and glyceride tricaprylate) is used, further more preferably, an ester of a straight-chain saturated fatty acid and a glycerin (tri [straight-chain fatty acid] glyceryl) is used, particularly preferably, a glyceryl tricaprylate is used.

When the first carboxylic acid ester is the ester of the fatty acid and the trihydric alcohol, the number of ester group per molecule is, for example, 1 or more, preferably 2 or more, more preferably 3.

These first carboxylic acid esters can be used alone or in combination of two or more. Preferably, the first carboxylic acid ester is used alone.

A saponification value Y of the first carboxylic acid ester is not particularly limited, and is, for example, 100 or more, preferably 250 or more, and for example, 500 or less, preferably 400 or less. The saponification value Y of the first carboxylic acid ester is, for example, obtained in accordance with the description of a neutralization titration method of JIS K0070 (1992) "Test methods for saponification value of chemical products". The saponification value Y of the first carboxylic acid ester is obtained by the following calculation formula when the molecular weight of the first carboxylic acid ester is already known.

Saponification value $Y=(1/\text{molecular weight})\times\text{number of ester group per molecule}\times56\times1000$ The ratio of the first carboxylic acid ester with respect to 100 parts by mass of the acrylic polymer is, for example, 30 parts by mass or more, preferably 50 parts by mass or more, and for example, 100 parts by mass or less, preferably 70 parts by mass or less. A content ratio B of the first carboxylic acid ester with respect to the resin composition (the pressure-sensitive adhesive layer 2) is, for example, 20 mass % or more, preferably 30 mass % or more, and for example, 70 mass % or less, preferably 50 mass % or less.

The pressure-sensitive adhesive composition can also contain a cross-linking agent as needed. The cross-linking agent is a cross-linking component that cross-links an acrylic polymer. Examples of the cross-linking agent include polyisocyanate compound, epoxy compound, melamine compound, peroxide compound, urea compound, metal alkoxide compound, metal chelate compound, metal salt compound, carbodiimide compound, oxazoline compound, aziridine compound, and amine compound. These cross-linking agents can be used alone or in combination of two or more. As the cross-linking agent, preferably, a polyisocyanate compound (polyfunctional isocyanate compound) is used. The ratio of the cross-linking agent with respect to 100 parts by mass of the acrylic polymer is, for example, 0.01 parts by mass or more, preferably 0.03 parts by mass or more, and for example, 10 parts by mass or less, preferably 1 part by mass or less.

The thickness of the pressure-sensitive adhesive layer 2 is, for example, 1 μm or more, preferably 10 μm or more, and for example, 200 μm or less, preferably 80 μm or less.

4. Substrate Layer

The substrate layer 3 is disposed at one side in the thickness direction of the pressure-sensitive adhesive layer 2. To be specific, the substrate layer 3 is disposed on the entire one-side surface in the thickness direction of the pressure-sensitive adhesive layer 2. That is, the substrate layer 3 is in contact with the one-side surface in the thickness direction of the pressure-sensitive adhesive layer 2. The substrate layer 3 has a generally flat plate (sheet) shape extending in the plane direction. In this manner, the substrate layer 3 supports the pressure-sensitive adhesive layer 2. The substrate layer 3 is prepared from a substrate composition.

The substrate composition contains, for example, a substrate resin and a second carboxylic acid ester.

The substrate resin is a main component in the substrate composition, and is, for example, a flexible resin that is capable of imparting appropriate elasticity, toughness, flexibility, and stretchability to the substrate layer 3.

The substrate resin is not particularly limited, and examples thereof include thermoplastic resins such as polyurethane resin, silicone resin, acrylic resin, polystyrene resin, vinyl chloride resin, and polyester resin. These substrate resins can be used alone or in combination of two or more.

The content ratio of the substrate resin with respect to the substrate composition (the substrate layer 3) is, for example, 97.5 mass % or less, preferably 95 mass % or less, more preferably 90 mass % or less, and for example, 70 mass % or more, preferably 80 mass % or more.

The second carboxylic acid ester is a transfer retardant that suppresses the transfer of the first carboxylic acid ester from the pressure-sensitive adhesive layer 2 to the substrate layer 3. As the second carboxylic acid ester, the same one as that in the above-described first carboxylic acid ester is used, and of those, the second carboxylic acid ester is appropriately selected in accordance with its use and purpose. As the second carboxylic acid ester, preferably, the same type of carboxylic acid ester as that in the first carboxylic acid ester is used. As the second carboxylic acid ester, preferably, a glyceryl trifatty acid ester is used. To be specific, preferably, both of the first carboxylic acid ester and the second carboxylic acid ester are the glyceryl trifatty acid ester. When both of the first carboxylic acid ester and the second carboxylic acid ester are the glyceryl trifatty acid ester, the stimuli to the skin at the time of the peeling can be furthermore suppressed, and the heat resistance can be further improved.

These second carboxylic acid esters can be used alone or in combination of two or more. Preferably, the second carboxylic acid ester is used alone.

A saponification value X of the second carboxylic acid ester is, for example, 100 or more, preferably 200 or more, more preferably 250 or more, and for example, 500 or less, preferably 400 or less.

The saponification value X of the second carboxylic acid ester is selected so that the ratio (X/Y) of the saponification value X of the second carboxylic acid ester to the saponification value Y of the first carboxylic acid ester is, for example, 0.5 or more, preferably 0.75 or more, and for example, 2 or less, preferably 1.5 or less.

When the above-described ratio (X/Y) of the saponification value of the second carboxylic acid ester to that of the first carboxylic acid ester is the above-described lower limit or more and the above-described upper limit or less, the properties of the second carboxylic acid ester are similar to or the same as those of the first carboxylic acid ester, so that the transfer of the first carboxylic acid ester from the pressure-sensitive adhesive layer 2 to the substrate layer 3 based on the second carboxylic acid ester can be effectively suppressed.

The saponification value X of the second carboxylic acid ester is obtained by the same method as that of the saponification value Y of the first carboxylic acid ester described above.

The ratio of the second carboxylic acid ester with respect to 100 parts by mass of the substrate resin is, for example, 1 part by mass or more, preferably 7 parts by mass or more, and for example, 50 parts by mass or less, preferably 25 parts by mass or less. A content ratio A of the second carboxylic acid ester with respect to the substrate composition (the substrate layer 3) is, for example, 2.5 mass % or more, preferably 5 mass % or more, more preferably 10 mass % or more, and for example, 30 mass % or less, preferably 20 mass % or less.

In a case where the ratio (the content ratio A) of the second carboxylic acid ester is the above-described lower limit or more, when the laminate patchable to a living body 1 is heated, the transfer of the first carboxylic acid ester from the pressure-sensitive adhesive layer 2 to the substrate layer 3 can be furthermore suppressed. Thus, the laminate patchable to a living body 1 has further more excellent heat resistance.

When the ratio (the content ratio A) of the second carboxylic acid ester is the above-described upper limit or less, occurrence of bleeding (precipitation) of the second carboxylic acid ester on the surface of the substrate layer 3 can be suppressed, and contamination toward the periphery caused by the bleeding (precipitation) and sticking of the substrate layer 3 to the periphery can be suppressed.

The second carboxylic acid ester is blended with the substrate resin so that the ratio (A/B) of the content ratio A of the second carboxylic acid ester with respect to the substrate layer 3 to the content ratio B of the first carboxylic acid ester with respect to the pressure-sensitive adhesive layer 2 is, for example, 0.1 or more, preferably 0.2 or more, and for example, 0.5 or less, preferably 0.45 or less.

In a case where the ratio (A/B) is the above-described lower limit or more, when the laminate patchable to a living body 1 is heated, the transfer of the first carboxylic acid ester from the pressure-sensitive adhesive layer 2 to the substrate layer 3 can be furthermore suppressed. Thus, the laminate patchable to a living body 1 has further more excellent heat resistance.

When the ratio (A/B) is the above-described upper limit or less, the occurrence of the bleeding (precipitation) of the second carboxylic acid ester on the surface of the substrate layer 3 can be suppressed, and the contamination toward the periphery caused by the bleeding (precipitation) and the sticking of the substrate layer 3 to the periphery can be suppressed.

The fracture elongation of the substrate layer 3 is, for example, 100% or more, preferably 200% or more, more preferably 300% or more, and for example, 2000% or less, preferably 1500% or less, more preferably 1000% or less. The measurement of the fracture elongation is described in Examples later. When the fracture elongation of the substrate layer 3 is the above-described lower limit or more, a reduction of the handling properties and a reduction of the strength can be suppressed.

The moisture permeability of the substrate layer 3 is, for example, 300 (g/m$^2$/day) or more, preferably 600 (g/m$^2$/day) or more, further more preferably 1000 (g/m$^2$/day) or more. When the moisture permeability of the substrate layer 3 is the above-described lower limit or more, in a case where the laminate patchable to a living body 1 is patched to the living body, a load to the living body can be suppressed.

The thickness of the substrate layer 3 is, for example, 1 μm or more, preferably 5 μm or more, and for example, 3000 μm (3 mm) or less, preferably 1000 μm or less.

When the thickness of the substrate layer 3 is the above-described lower limit or more, the shape of the substrate layer 3 can be surely retained. Thus, the laminate patchable to a living body 1 including the substrate layer 3 has excellent handleability.

When the thickness of the substrate layer 3 is the above-described upper limit or less, the substrate layer 3 can be surely patched to the living body, and inconvenience is hardly felt in a state of patching the laminate patchable to a living body 1 to the skin.

The ratio (thickness of the substrate layer 3/thickness of the pressure-sensitive adhesive layer 2) of the thickness of the substrate layer 3 to that of the pressure-sensitive adhesive layer 2 is, for example, 0.005 or more, preferably 0.06 or more, and for example, 3000 or less, preferably 100 or less.

5. Backing Film

The backing film 5 is the one-side layer in the thickness direction that forms the one-side surface in the thickness direction in the laminate patchable to a living body 1. The backing film 5 is in contact with the entire one-side surface in the thickness direction of the substrate layer 3. The backing film 5 has a generally flat plate (sheet) shape extending in the plane direction. The backing film 5 consists of a film capable of flexibly supporting the substrate layer 3. Also, the backing film 5 is a protecting layer that protects the one-side surface in the thickness direction of the substrate layer 3. The backing film 5 is a film that is used for fabricating the substrate layer 3, and a peeling layer (second peeling layer) that is peeled from the substrate layer 3 at the time of the use of the laminate patchable to a living body 1. Examples of the backing film 5 include resin films including polyester films such as PET and metal foils such as stainless steel foil. Preferably, a resin film is used, more preferably, a polyester film is used. The thickness of the backing film 5 is, for example, 1 μm or more, preferably 10 μm or more, and for example, 200 μm or less, preferably 100 μm or less.

6. Fabrication Method of Laminate Patchable to Living Body

To fabricate the laminate patchable to a living body 1, first, the peeling layer 4 is prepared. Subsequently, the pressure-sensitive adhesive layer 2 is fabricated on the surface of the peeling layer 4.

To fabricate the pressure-sensitive adhesive layer 2, first, the pressure-sensitive adhesive composition is prepared from the acrylic polymer and the first carboxylic acid ester. To be specific, the acrylic polymer and the first carboxylic acid ester, and, if necessary, the cross-linking agent are blended to be mixed, so that the pressure-sensitive adhesive composition (pressure-sensitive adhesive layer coating liquid) is prepared. Next, the pressure-sensitive adhesive composition is applied to the surface of the peeling layer 4 to be subsequently dried by heating. The drying temperature is, for example, 100° C. or more and 150° C. or less, and the drying time is, for example, 1 minute or more and 15 minutes or less.

Thereafter, when the pressure-sensitive adhesive composition contains the cross-linking agent, the dried pressure-sensitive adhesive composition is further heated (aged). The aging temperature is, for example, 30° C. or more and 80° C. or less, and the aging time is, for example, 1 hour or more and 100 hours or less.

In this manner, the pressure-sensitive adhesive layer 2 is fabricated on the surface of the peeling layer 4.

Separately, the backing film 5 is prepared. Subsequently, the substrate layer 3 is fabricated on the surface of the backing film 5.

To fabricate the substrate layer 3, a substrate composition is prepared from the substrate resin and the second carboxylic acid ester. To be specific, the substrate resin, the second carboxylic acid ester, and the solvent are blended to be mixed, so that a solution of the substrate composition (substrate coating liquid) is prepared. The solvent is not particularly limited, and for example, organic solvents including ketone solvents such as methyl ethyl ketone and aprotic polar solvents such as dimethylformamide are used. These solvents can be used alone or in combination of two or more. When the substrate resin is prepared as a solution obtained by being dissolved in the solvent in advance, the solvent contained in the above-described solution is used as it is, and the second carboxylic acid ester is blended with the solution, that is, the substrate coating liquid may be prepared without separately adding the solvent. The mixing ratio of the solvent is adjusted so that the ratio of the substrate resin with respect to the substrate coating liquid is, for example, 5 mass % or more, preferably 10 mass % or more, and for example, 75 mass % or less, preferably below 50 mass %.

Next, the substrate coating liquid is applied to the surface of the backing film 5.

After the application, the substrate coating liquid is dried.

The drying conditions are the conditions capable of removing the solvent. The drying temperature is, for example, 90° C. or more, preferably 110° C. or more, and for example, 150° C. or less, preferably 130° C. or less. The drying time is, for example, 1 minute or more, preferably 3 minutes or more, and for example, 30 minutes or less, preferably 10 minutes or less.

In this manner, the substrate layer 3 that is supported by the backing film 5 is fabricated.

Thereafter, the pressure-sensitive adhesive layer 2 and the substrate layer 3 are stuck to each other by, for example, a laminator or the like. To be specific, the pressure-sensitive adhesive layer 2 and the substrate layer 3 are brought into contact with each other.

In this manner, the laminate patchable to a living body 1 including the peeling layer 4, the pressure-sensitive adhesive layer 2, the substrate layer 3, and the backing film 5 is fabricated.

7. Modified Examples

In the above-described one embodiment, as shown in FIG. 1, the laminate patchable to a living body 1 includes the peeling layer 4 and the backing film 5 in addition to the pressure-sensitive adhesive layer 2 and the substrate layer 3.

Figure 2:
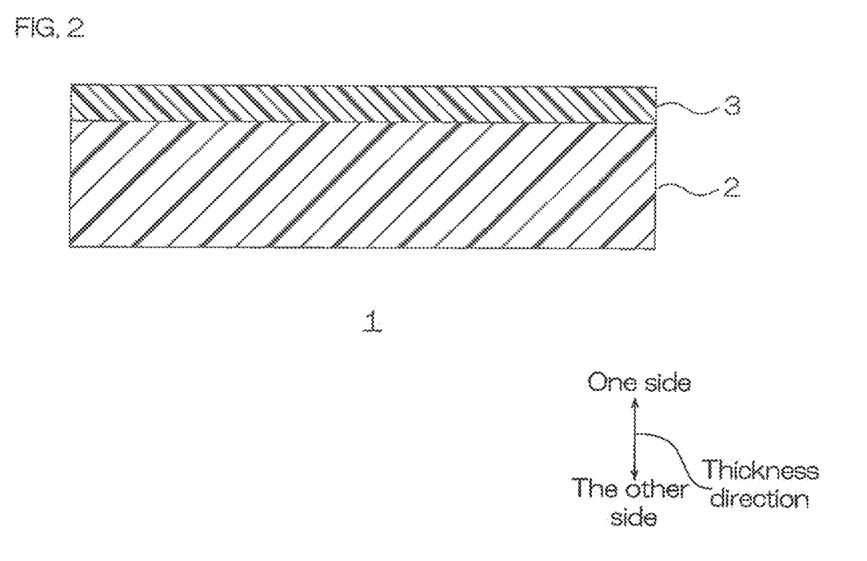
FIG. 2 shows a cross-sectional view of a modified example (embodiment without including a peeling layer and a backing film) of the laminate patchable to a living body shown in FIG. 1.

As shown in FIG. 2, however, the laminate patchable to a living body 1 can also include only the pressure-sensitive adhesive layer 2 and the substrate layer 3 without including the peeling layer 4 (ref: FIG. 1) and the backing film 5 (ref: FIG. 1).

In the laminate patchable to a living body 1 shown in FIG. 2, the pressure-sensitive adhesive layer 2 is the other-side layer in the thickness direction that forms the other-side surface in the thickness direction of the laminate patchable to a living body 1, and the substrate layer 3 is the one-side layer in the thickness direction that forms the other-side surface in the thickness direction of the laminate patchable to a living body 1.

Of the peeling layer 4 and the backing film 5, the laminate patchable to a living body 1 can also include only one of them.

Although not shown, for example, the laminate patchable to a living body 1 can sequentially include the backing film 5, the substrate layer 3, and the pressure-sensitive adhesive layer 2 without including the peeling layer 4. To fabricate the laminate patchable to a living body 1, for example, the pressure-sensitive adhesive layer 2 is directly formed on the surface of the substrate layer 3. To be specific, the pressure-sensitive adhesive composition (pressure-sensitive adhesive layer coating liquid) is directly applied to the surface of the substrate layer 3 that is supported by the backing film 5. Thereafter, the pressure-sensitive adhesive composition is dried, and if necessary, aged. In this manner, though not shown, the laminate patchable to a living body 1 sequentially including the backing film 5, the substrate layer 3, and the pressure-sensitive adhesive layer 2 at the other side in the thickness direction can be obtained.

Also, though not shown, the laminate patchable to a living body 1 can sequentially include the peeling layer 4, the pressure-sensitive adhesive layer 2, and the substrate layer 3 without including the backing film 5. To produce the laminate patchable to a living body 1, for example, the substrate layer 3 is directly formed on the surface of the pressure-sensitive adhesive layer 2. To be specific, the substrate coating liquid is directly applied to the surface of the pressure-sensitive adhesive layer 2 that is supported by the peeling layer 4. Thereafter, the substrate coating liquid is dried. In this manner, the laminate patchable to a living body 1 sequentially including the peeling layer 4, the pressure-sensitive adhesive layer 2, and the substrate layer 3 at one side in the thickness direction can be obtained.

Also, the laminate patchable to a living body 1 includes the pressure-sensitive adhesive layer 2 and the substrate layer 3. Although not shown, for example, the laminate patchable to a living body 1 can also further include various additional members such as ink layer and circuit layer. In the modified example, the laminate patchable to a living body 1 includes, for example, an additional member that is disposed on the one-side surface in the thickness direction of the substrate layer 3. The laminate patchable to a living body 1 can also include the above-described additional member that is disposed in the middle portion in the thickness direction of the laminate patchable to a living body 1; can also include, for example, the additional member that is embedded in the pressure-sensitive adhesive layer 2 and/or the substrate layer 3; and furthermore, can also include the additional member that is interposed on the border between the pressure-sensitive adhesive layer 2 and the substrate layer 3.

8. Use of Laminate Patchable to Living Body

The laminate patchable to a living body 1 is used for patching to the living body.

The living body is not particularly limited. Examples of the living body include animal body and plant body. Examples of the animal body include human body (human) and domestic animals such as cow, horse, pig, chicken, dog, and cat. Examples of the plant body include grains such as rice, barley, wheat, corn, and sugarcane; crops that form root stocks or tuberous roots such as potato and sweet potato; leguminous plants such as soybean, kidney bean, broad bean, and garden pea; seed plants such as peanut, sesame, rapeseed, cotton seed, sunflower, and safflower; and crops having a fruit such as apple, melon, and grapes. As the living body, preferably, an animal body is used, more preferably, a human body is used.

The laminate patchable to a living body 1 is, for example, used for various uses including medical use and sanitary material use, and to be specific, is used as a bandage or the like.

To be specific, when the laminate patchable to a living body 1 includes the peeling layer 4, first, the peeling layer 4 is peeled from the pressure-sensitive adhesive layer 2, and subsequently, the other-side surface in the thickness direction of the pressure-sensitive adhesive layer 2 is patched to the living body. To be specific, the substrate layer 3 is patched to the living body via the pressure-sensitive adhesive layer 2.

Thereafter, when the laminate patchable to a living body 1 includes the backing film 5, first, the backing film 5 is peeled from the substrate layer 3. In this manner, the one-side surface in the thickness direction of the substrate layer 3 is exposed outwardly.

9. Function and Effect of Laminate Patchable to Living Body

The laminate patchable to a living body 1 may be required to have excellent heat resistance. To be specific, when the above-described each of the members is provided in the laminate patchable to a living body 1, for example, as in a wire-formed layer of a wearable device, excellent heat resistance of not easily deforming the above-described member after heating at the time of the formation of the wire is required. An example of the wearable device includes a living body patch-type sensor including a stretchable main body portion and a stretchable electronic circuit described in Japanese Translation of PCT International Application Publication No. 2012-508984.

As in the ink layer in the laser marking film described in WO 2012/008278, even when the substrate layer 3 is heated based on the application of a laser beam, laser marking images showing various information such as bar codes and characters need to be accurately read. Thus, excellent heat resistance of not easily deforming the substrate layer 3 by heating is required in the laminate patchable to a living body 1.

Figure 4:
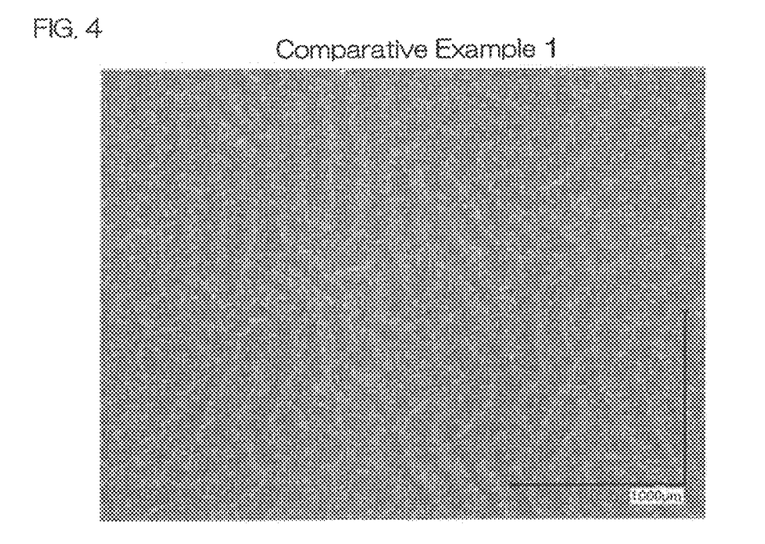
FIG. 4 shows an image processing view of a picture of a laminate patchable to a living body of Comparative Example 1 when viewed from the top.

However, the pressure-sensitive adhesion sheet described in Patent Document 1 includes the film and the pressure-sensitive adhesion layer that is formed from the resin composition containing an acrylic acid ester polymer. Thus, there is a disadvantage that when the pressure-sensitive adhesion sheet is heated, to be specific, when the pressure-sensitive adhesion layer is heated, the carboxylic acid ester is transferred into the film, and the film swells based on the transfer, so that the deformation such as wrinkles occurs in the film (ref: FIG. 4), and thus, the above-described information cannot be exactly read.

Meanwhile, when the laminate patchable to a living body 1 is heated, to be specific, when the pressure-sensitive adhesive layer 2 is heated, the substrate layer 3 contains the second carboxylic acid ester, so that the transfer of the first carboxylic acid ester into the substrate layer 3 can be suppressed. That is, the transfer of the first carboxylic acid ester in the pressure-sensitive adhesive layer 2 into the substrate layer 3 can be suppressed. Thus, the deformation such as wrinkles in the substrate layer 3 based on the transfer of the first carboxylic acid ester can be suppressed. That is, the laminate patchable to a living body 1 has excellent heat resistance.

As a result, the above-described information can be exactly read.

In the laminate patchable to a living body 1, in a case where the ratio (A/B) of the content ratio A of the second carboxylic acid ester with respect to the substrate layer 3 to the content ratio B of the first carboxylic acid ester with respect to the pressure-sensitive adhesive layer 2 is 0.1 or more, when the laminate patchable to a living body 1 is heated, the transfer of the first carboxylic acid ester from the pressure-sensitive adhesive layer 2 to the substrate layer 3 can be furthermore suppressed. Thus, the laminate patchable to a living body 1 has further more excellent heat resistance.

Also, when the ratio (A/B) is 0.5 or less, the occurrence of the bleeding (precipitation) of the second carboxylic acid ester on the surface of the substrate layer 3 can be suppressed, and the contamination toward the periphery caused by the bleeding (precipitation) and the sticking of the substrate layer 3 to the periphery can be suppressed.

In the laminate patchable to a living body 1, in a case where the content ratio A of the second carboxylic acid ester with respect to the substrate layer 3 is 5 mass % or more, when the laminate patchable to a living body 1 is heated, the transfer of the first carboxylic acid ester from the pressure-sensitive adhesive layer 2 to the substrate layer 3 can be furthermore suppressed. Thus, the laminate patchable to a living body 1 has further more excellent heat resistance.

Furthermore, in the laminate patchable to a living body 1, when the first carboxylic acid ester and the second carboxylic acid ester are the glyceryl trifatty acid ester, the stimuli to the skin at the time of the peeling can be furthermore suppressed, and the heat resistance can be further improved.

In the laminate patchable to a living body 1, when the thickness of the substrate layer 3 is 1 μm or more, the shape of the substrate layer 3 can be surely retained. Thus, the laminate patchable to a living body 1 has excellent handleability. Also, when the thickness of the substrate layer 3 is 3 mm or less, the conformability of the substrate layer 3 can be ensured, and the substrate layer 3 can be surely patched to the living body. Also, the inconvenience is hardly felt in a state of patching the laminate patchable to a living body 1 to the skin.

In the laminate patchable to a living body 1, when the ratio (X/Y) of the saponification value X of the second carboxylic acid ester to the saponification value Y of the first carboxylic acid ester is 0.5 or more and 2 or less, the properties of the second carboxylic acid ester are similar to or the same as those of the first carboxylic acid ester, and when the laminate patchable to a living body 1 is heated, the transfer of the first carboxylic acid ester from the pressure-sensitive adhesive layer 2 to the substrate layer 3 can be furthermore suppressed. Thus, the laminate patchable to a living body 1 has further more excellent heat resistance.

EXAMPLES

Next, the present invention is further described based on Examples and Comparative Example. The present invention is however not limited by the following Examples and Comparative Example. The specific numerical values in mixing ratio (content ratio), property value, and parameter used in the following description can be replaced with upper limit values (numerical values defined as "or less" or "below") or lower limit values (numerical values defined as "or more" or "above") of corresponding numerical values in mixing ratio (content ratio), property value, and parameter described in the above-described "DESCRIPTION OF EMBODIMENTS".

Example 1

1. Fabrication of Pressure-Sensitive Adhesive Layer

In accordance with the description of Example 1 in Japanese Unexamined Patent Publication No. 2003-342541, an acrylic polymer was prepared from an isononyl acrylate (iNA), a methoxyethyl acrylate (MEA), and an acrylic acid (AA).

Next, 100 parts by mass of acrylic polymer, 60 parts by mass of glyceryl tricaprylate (saponification value Y of 355) as the first carboxylic acid ester, and 0.04 parts by mass of Coronate HL (trade name, polyfunctional isocyanate compound, manufactured by Nippon Polyurethane Industry Co., Ltd.) as a cross-linking agent were blended to be stirred and mixed, so that a pressure-sensitive adhesive layer coating liquid (pressure-sensitive adhesive composition) was prepared. Thereafter, the pressure-sensitive adhesive layer coating liquid was applied to the surface of a PET film as the peeling layer 4 in which the surface thereof was subjected to peeling treatment so that the thickness thereof after drying was 25 μm. Thereafter, the applied surface was dried at 120° C. for 3 minutes. The pressure-sensitive adhesive layer 2 was heated at 60° C. for 72 hours to be aged. In this manner, the pressure-sensitive adhesive layer 2 that was supported by the peeling layer 4 was fabricated.

2. Fabrication of Substrate Layer

A polyether urethane solution (trade name: "T-8180N", 20 mass % solution of polyether urethane (solvent=methyl ethyl ketone:dimethylformamide=1:1), manufactured by DIC Covestro Polymer Ltd.) and the glyceryl tricaprylate (saponification value X of 355) as the second carboxylic acid ester were blended at a normal temperature so that the mass ratio of the polyether urethane to the glyceryl tricaprylate was 100/5 to be then stirred and mixed, so that a substrate layer coating liquid was prepared. Thereafter, the substrate layer coating liquid was applied to the surface of the PET film as the backing film 5 in which the surface thereof was subjected to peeling treatment so that the thickness thereof after drying was 8 μm to be then dried at 120° C. for 5 minutes. In this manner, the substrate layer 3 that was supported by the backing film 5 was fabricated.

In the substrate layer 3 from which the backing film 5 was peeled, the fracture elongation of the substrate layer 3 was measured at a tensile rate of 5 mm/min with a test piece type 2 in conformity with JIS K 7127 (1999), and the result was 750%.

In the substrate layer 3 from which the backing film 5 was peeled, the moisture permeability of the substrate layer 3 was measured under the condition A in conformity with JIS Z 0208 (1976), and the result was 2500 (g/m$^2$/day).

3. Fabrication of Laminate Patchable to Living Body

The pressure-sensitive adhesive layer 2 and the substrate layer 3 were stuck to each other at 60° C. by a vacuum laminator.

In this manner, the laminate patchable to a living body 1 sequentially including the peeling layer 4, the pressure-sensitive adhesive layer 2, the substrate layer 3, and the backing film 5 was fabricated.

Examples 2 to 5

The substrate layer 3 was fabricated in accordance with the mixing formulation described in Table 1, and subsequently, the laminate patchable to a living body 1 was fabricated in the same manner as that of Example 1.

Comparative Example 1

A laminate patchable to a living body of Comparative Example 1 was fabricated in the same manner as that of Example 1, except that the second carboxylic acid ester was not blended with the substrate layer coating liquid in "1. Fabrication of Substrate Layer".

<Evaluation of Heat Resistance>

The following items are evaluated in each Example and Comparative Example, and the results are shown in Table 1.

1. Presence or Absence of Wrinkle

The laminate patchable to a living body 1 from which the backing film 5 was peeled was heated at 110° C. for 1 hour.

Thereafter, the surface (one-side surface in the thickness direction) of the substrate layer 3 was observed with a digital microscope (manufactured by KEYENCE CORPORATION), and evaluated with the following criteria.

Presence: wrinkle was observed on the surface.

Absence: wrinkle was not observed on the surface.

Figure 3:
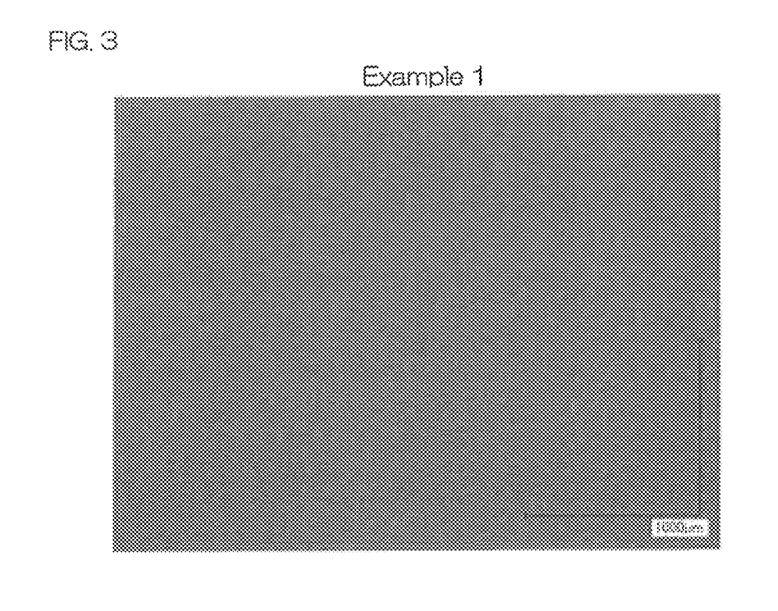
FIG. 3 shows an image processing view of a picture of a laminate patchable to a living body of Example 1 when viewed from the top.

In Example 1 and Comparative Example 1, pictures observed on the surface (one-side surface in the thickness direction) of the substrate layer 3 are taken with the digital microscope (manufactured by KEYENCE CORPORATION), and the results are shown in FIGS. 3 and 4.

2. Surface Roughness Sa

The laminate patchable to a living body 1 from which the backing film 5 was peeled was heated at 110° C. for 1 hour.

Thereafter, the surface (one-side surface in the thickness direction) of the substrate layer 3 was measured with a laser microscope (manufactured by KEYENCE CORPORATION), and the surface roughness Sa was measured.

TABLE 1

| | | | | Saponification Value | Ex. 1 | Ex. 2 | Ex. 3 | Ex. 4 | Ex. 5 | Comp. Ex. 1 |
|---|---|---|---|---|---|---|---|---|---|---|
| Substrate Composition | Substrate Resin | Polyether Urethane | | | 100 | 100 | 100 | 100 | 100 | 100 |
| | Second Carboxylic Acid Ester | Glyceryl Tricaprylate | X | 355 | 5 | 10 | 20 | 10 | — | — |
| | | Isopropyl Myristate | | 205 | — | — | — | — | 10 | — |
| | Content Ratio of Second Carboxylic Acid Ester | A mass % (VS Substrate) | | | 4.8 | 9.1 | 16.7 | 9.1 | 9.1 | — |
| Pressure-Sensitive Adhesive Composition | Acrylic Polymer | INA/MEA/AA = 65:30:5 | | | 100 | 100 | 100 | 100 | 100 | 100 |
| | First Carboxylic Acid Ester | Glyceryl Tricaprylate | Y | 355 | 60 | 60 | 60 | — | 60 | 60 |
| | | Isopropyl Myristate | | 205 | — | — | — | 80 | — | — |
| | Cross-Linking Agent | Polyfunctional Isocyanate Compound | | | 0.04 | 0.04 | 0.04 | 0.04 | 0.04 | 0.04 |
| | Content Ratio of First Carboxylic Acid Ester | B mass % (VS Pressure-Sensitive Adhesive) | | | 37.5 | 37.5 | 37.5 | 44.4 | 37.5 | 37.5 |
| | Ratio of Content Ratio of First Carboxylic Acid Ester to That of Second Carboxylic Acid Ester | A/B | | | 0.13 | 0.24 | 0.44 | 0.20 | 0.24 | — |
| | Ratio of Saponification Value of First Carboxylic Acid Ester to That of Second Carboxylic Acid Ester | X/Y | | | 1.0 | 1.0 | 1.0 | 1.7 | 0.6 | — |
| Evaluation Result | Heat Resistance Evaluation (110° C., 1 hr) | Presence or Absence of Occurrence of Wrinkles in Substrate | | | Absence | Absence | Absence | Absence | Absence | Presence |
| | | Surface Roughness of Substrate (Sa) μm | | | 1.5 | 0.5 | 0.5 | 0.7 | 0.8 | 28 |

INDUSTRIAL APPLICABILITY

The laminate patchable to a living body is used by patching to the living body.

While the illustrative embodiments of the present invention are provided in the above description, such is for illustrative purpose only and it is not to be construed as limiting the scope of the present invention. Modification and variation of the present invention that will be obvious to those skilled in the art is to be covered by the following claims.

DESCRIPTION OF REFERENCE NUMERALS

1 Laminate patchable to a living body
2 Pressure-sensitive adhesive layer
3 Substrate layer

The invention claimed is:

1. A laminate patchable to a living body comprising:
   a pressure-sensitive adhesive layer for patching to the living body; and
   a substrate layer disposed on a one-side surface in a thickness direction of the pressure-sensitive adhesive layer and supporting the pressure-sensitive adhesive layer,
   wherein:
   the pressure-sensitive adhesive layer contains a first carboxylic acid ester,
   the substrate layer contains a second carboxylic acid ester, the ratio (A/B) of a content ratio A of the second carboxylic acid ester with respect to the substrate layer to a content ratio B of the first carboxylic acid ester with respect to the pressure-sensitive adhesive layer is 0.2 or more and 0.5 or less, and the thickness of the substrate layer is 1 μm or more and 8 μm or less.

2. The laminate patchable to a living body according to claim 1, wherein the content ratio A of the second carboxylic acid ester with respect to the substrate layer is 5 mass % or more.

3. The laminate patchable to a living body according to claim 1, wherein the first carboxylic acid ester and the second carboxylic acid ester are a glyceryl trifatty acid ester.

4. The laminate patchable to a living body according to claim 1, wherein the ratio (X/Y) of a saponification value X of the second carboxylic acid ester to a saponification value Y of the first carboxylic acid ester is 0.5 or more and 2 or less.

\* \* \* \* \*